United States Patent
Harris et al.

(10) Patent No.: US 7,341,571 B1
(45) Date of Patent: Mar. 11, 2008

(54) BALLOON CATHETER HAVING A MULTILAYERED DISTAL TIP

(75) Inventors: Mark E. Harris, Temecula, CA (US); Vincent P. Bavaro, Temecula, CA (US); Kenneth Wantink, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 515 days.

(21) Appl. No.: 10/932,620

(22) Filed: Sep. 2, 2004

(51) Int. Cl.
*A61M 29/00* (2006.01)

(52) U.S. Cl. .................................. 604/96.01

(58) Field of Classification Search .......... 604/96.01, 604/103, 103.06, 509, 101.01–101.05, 915, 604/916, 920; 606/191–194
See application file for complete search history.

(56) References Cited

U.S. PATENT DOCUMENTS

| | | | |
|---|---|---|---|
| 4,636,346 A | 1/1987 | Gold et al. | |
| 5,256,145 A * | 10/1993 | Atkinson et al. | 604/103.01 |
| 5,445,624 A | 8/1995 | Jimenez | |
| 5,571,087 A | 11/1996 | Ressemann et al. | |
| 5,811,043 A | 9/1998 | Horrigan et al. | |
| 5,961,765 A * | 10/1999 | Kastenhofer | 156/244.13 |
| 6,010,521 A | 1/2000 | Lee et al. | |
| 6,319,228 B1 | 11/2001 | Kastenhofer | |
| 6,325,790 B1 | 12/2001 | Trotta | |
| 6,368,301 B1 | 4/2002 | Hamilton et al. | |
| 6,403,011 B1 | 6/2002 | Stamberg | |
| 6,464,683 B1 | 10/2002 | Samuelson et al. | |
| 6,530,938 B1 * | 3/2003 | Lee et al. | 606/194 |
| 6,589,215 B2 | 7/2003 | Yang et al. | |
| 6,591,472 B1 | 7/2003 | Noone et al. | |
| 6,610,068 B1 | 8/2003 | Yang | |
| 6,623,504 B2 | 9/2003 | Vrba et al. | |
| 6,692,461 B2 | 2/2004 | Wantink | |
| 6,918,920 B1 | 7/2005 | Wang et al. | |
| 6,960,186 B1 | 11/2005 | Fukaya et al. | |
| 7,048,713 B2 * | 5/2006 | Wang | 604/96.01 |
| 2002/0072705 A1 | 6/2002 | Vrba et al. | |
| 2003/0199849 A1 | 10/2003 | Hackett | |
| 2005/0131445 A1 | 6/2005 | Holman et al. | |

* cited by examiner

*Primary Examiner*—Manuel Mendez
(74) *Attorney, Agent, or Firm*—Fulwider Patton LLP

(57) ABSTRACT

A catheter having a distal tip with an inner layer formed of a polymeric material having a coefficient of friction and surface energy which are relatively low, such that the inner layer has a lubricious, non-polar inner surface repulsive to polar liquids. As a result, blood coagulation in the distal tip, and adherence of the distal tip on the guidewire are prevented or minimized.

20 Claims, 1 Drawing Sheet

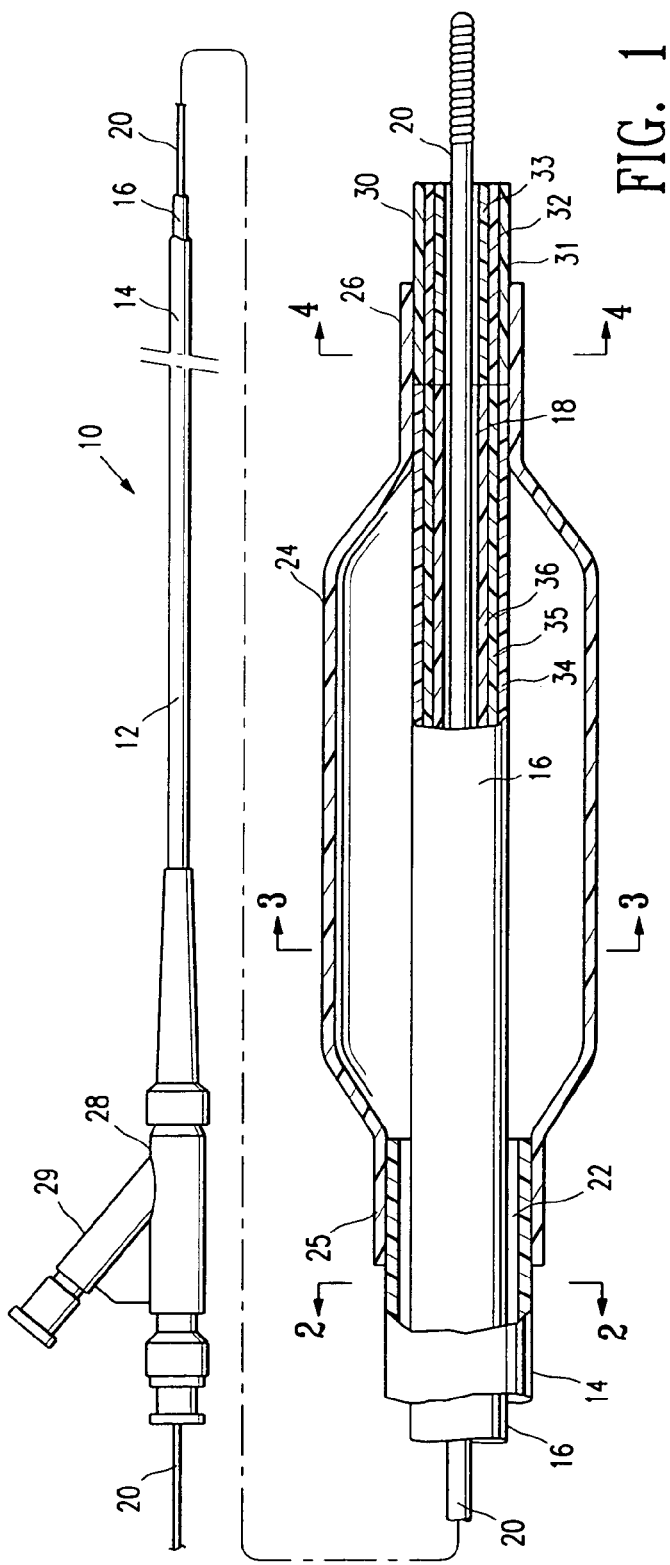
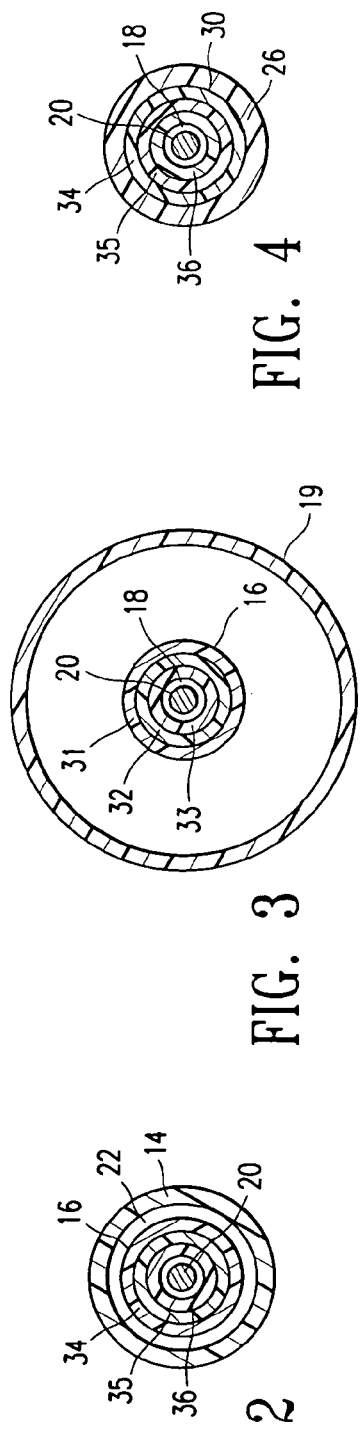
FIG. 1
FIG. 2
FIG. 3
FIG. 4

BALLOON CATHETER HAVING A MULTILAYERED DISTAL TIP

BACKGROUND OF THE INVENTION

This invention relates generally to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter must have good crossability (i.e., the ability of the catheter distal end to cross stenosed portions of the vascular anatomy).

Conventional intravascular catheters have commonly included a soft distal tip to prevent or minimize injury to the vessel during advancement of the catheter therein. Additionally, it is necessary to minimize the stiffness of the distal end of the catheter to aid in flexibly tracking the device during dilatation and stenting procedures. One difficulty has been the tendency of small agglomerations of blood and contrast media to adhere to the soft tip materials and make it difficult to advance or retract the catheter.

Accordingly, it would be a significant advance to provide a catheter with a soft tip having improved performance. This invention satisfies these and other needs.

SUMMARY OF THE INVENTION

The invention is directed to a catheter having a distal tip with an inner layer formed of a polymeric material having a coefficient of friction and surface energy which are relatively low, such that the inner layer has a lubricious, non-polar inner surface repulsive to polar liquids. As a result, blood coagulation in the distal tip, and adherence of the distal tip on the guidewire are prevented or minimized.

The catheter is preferably a balloon catheter, generally comprising an elongated shaft having an inflation lumen and a guidewire lumen, and a balloon on a distal shaft section with an interior in fluid communication with the inflation lumen, with the distal tip at the catheter distal end. The distal tip defines a lumen therein in communication with the guidewire lumen of the shaft.

The distal tip typically has an outer layer secured to an outer surface of the inner layer or to a middle layer located between the inner and outer layers. The inner layer of the distal tip has a lower coefficient of friction than the outer layer, to provide a lubricious inner surface which minimizes drag on the guidewire. Additionally, the inner layer preferably has a lower surface energy than the outer layer and a non-polar surface. As a result, the wettability of the inner surface of the distal tip by polar liquids such as water and blood is poor and blood coagulation in the distal tip is minimized. In contrast, conventional soft tips formed of low durometer polar polymers such as polyamide elastomers are tacky at body temperature due to the relatively low glass transition temperature of the material, and can have a relatively high surface energy with an affinity for polar fluids such as blood.

In a presently preferred embodiment, the inner layer is formed of a polymeric material which has a non-polar surface (without requiring an additive to provide the non-polar surface) with a surface energy of not greater than about 31 dynes/cm at 20° C., and a static coefficient of friction of not greater than about 0.20 and a kinetic coefficient of friction of not greater than about 0.14. Additionally, the preferred inner layer material is relatively ductile and bondable, and is melt processable. The preferred inner layer materials have an elongation of at least 50% and a tensile strength of about 3200 to about 4500 psi. Additionally, the preferred inner layer materials are not overly stiff, and thus have a flexural modulus of not greater than about 250 kpsi at room temperature. However, the modulus of the polymeric material forming the inner layer is typically relatively high compared to the outer layer, so that the overall flexibility and softness of the distal tip is enhanced by the flexible outer layer.

A variety of suitable materials may be used for the inner layer including homopolymers and copolymers of high, mid, linear low, and low density polyethylene (HDPE, MDPE, LLDPE, and LDPE), copolymers of propylene (PP), metallocene polyolefin elastomers such as Affinity, fluoropolymers such as polytetrafluoroethylene (PTFE), melt processable fluoropolymers such as FEP, PFA, PVDF, PFE, and TEFZEL.

A presently preferred inner layer material is HDPE homopolymer. The relatively high lubricity of HDPE makes it preferable to the other polyolefins listed above. Materials such as PTFE having a relatively high stiffness and cost, poor bondability, and non-melt processability are not preferred to HDPE. A distal tip may break when subjected to a pulling or deforming force if the polymeric material forming the distal tip is overly stiff and brittle. Therefore, materials such as ultrahigh molecular weight polyethylene are not preferred due to the brittle nature and poor melt processability of the material. However, a fractional melt, high load HDPE this is melt processable can be used as the distal tip inner layer.

The outer layer of the distal tip is preferably formed of a flexible polymer. Additionally, the outer layer preferably provides a bondable surface for bonding the distal tip to another component of the catheter such as the catheter balloon. A variety of suitable materials may be used for the outer layer including polyamide homopolymers and copolymers of Nylon 11 and 12 like Pebax and Vestamid family resin grades, polyurethanes such as polyesterurethane and polyetherurethanes like Pellethane and Texin family resin grades, polyesters such as PET, PBT and copolyesters such as Hytrel and Arnitel family resin grades, olefin derived copolymers, natural and synthetic rubbers such as silicone and Santoprene, thermoplastic elastomers such as Kraton, and specialty polymers such as ionomers. A presently preferred outer layer material is Polyether block amide (Pebax), preferably having a Shore durometer hardness of about 25D to about 63D.

The distal tip must be flexible and soft enough to be atraumatic and allow for tracking the catheter on a guidewire in the patient's vessels during a medical procedure. The distal tip is typically softer and more flexible than the portion of the shaft proximally adjacent to the distal tip which defines the guidewire lumen in communication with the distal tip lumen. In one embodiment, the proximally adjacent portion of the shaft has an outer layer with a higher flexural modulus than the outer layer of the distal tip.

In one embodiment, the distal tip includes one or more additional layers to improve bonding between the inner and outer layers or to impart other characteristics to the distal tip. For example, in a presently preferred embodiment, the distal tip has a middle layer comprising an adhesive tie layer resin which fixedly bonds the inner layer to the outer layer. Absent the middle layer(s), the inner layer is directly fixedly secured to the outer layer of the distal tip. Preferably, each layer of the distal tip is formed of a melt processable material, which therefore can be extruded to form the tubular shape of the distal tip.

The distal tip of the invention provides an improved combination of characteristics so that the distal tip is soft, conformable, atraumatic, and with a low friction inner surface that is able to repel small agglomerations of blood and contrast media. The relatively low coefficient of friction of the inner layer provides for a low friction mechanical interaction between the guidewire and the distal tip inner surface. Additionally, the relatively low surface energy, non-polar surface repels blood and contrast media. These and other advantages of the invention will become more apparent from the following detailed description and exemplary drawings.

BRIEF DESCRIPTION OF THE DRAWINGS

FIG. 1 is an elevational view partially in section of a balloon catheter embodying features of the invention.

FIGS. 2-4 are transverse cross sectional views of the balloon catheter of FIG. 1, taken along lines 2-2, 3-3, and 4-4, respectively.

DETAILED DESCRIPTION OF THE PREFERRED EMBODIMENTS

FIG. 1 illustrates an over-the-wire type balloon catheter 10 embodying features of the invention. Catheter 10 generally comprises an elongated catheter shaft 12, an inflatable balloon 24 on a distal shaft section, and a distal tip 30 at the catheter distal end. In the illustrated embodiment, the shaft comprises an outer tubular member 14 defining an inflation lumen 22 therein, and an inner tubular member 16 defining a guidewire lumen 18 therein configured to slidingly receive a guidewire 20. Specifically, in the illustrated embodiment, the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2-2. In the embodiment illustrated in FIG. 1, the guidewire lumen 18 extends to the proximal end of the catheter. Inflatable balloon 24 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 28 at the proximal end of catheter shaft 12 is configured to provide access to guidewire lumen 18, and to direct inflation fluid through arm 29 into inflation lumen 22. The balloon 24 is illustrated in an inflated configuration in FIG. 1. The distal end of catheter 10 may be advanced to a desired region of the patient's body lumen in a conventional manner with the balloon in a deflated configuration, and the balloon 24 inflated by directing inflation fluid into the balloon interior to perform a medical procedure such as dilatation or delivery of a stent (not shown).

The distal tip 30 defines a lumen therein which is in communication with the guidewire lumen 18 in the inner tubular member 16, and which extends to a guidewire distal port in the distal end of the distal tip 30. The proximal end of the distal tip is bonded to the distal end of the inner tubular member 16 with a butt-joint, and the distal skirt section 26 of the balloon 24 is bonded to the outer surfaces of the distal tip 30 and the inner tubular member 16. However, a variety of suitable configurations can be used for securing the distal tip at the catheter distal end as are conventionally known.

The distal tip 30 has an inner layer 31, an outer layer 33, and a middle layer 32 between the inner and outer layers 31, 33. The inner layer 31 of the distal tip 30 comprises a non-polar polymeric material having a relatively low coefficient of friction and a relatively low surface energy, so that the inner layer is repellant to polar fluids such as blood. Typically the coefficient of friction and surface energy of the inner layer 31 are lower than those of the outer layer 33 and the middle layer 32. In a presently preferred embodiment, the inner layer 31 of the distal tip 30 is formed of high density polyethylene homopolymer (HDPE), which is a non-polar polymer having a surface energy of about 31 dynes/cm at 20° C., a static coefficient of friction of about 0.18, and a kinetic coefficient of friction of about 0.08-0.12. HDPE is melt processable so that it can be melt co-extruded into the tubular shape of distal tip 30 together with the middle and outer layers 32, 33. Additionally, HDPE is relatively ductile (i.e., elongation at yield and break of greater than about 60%), and bondable (e.g., miscible with other polymers conventionally used in catheter construction). For example, HDPE is fusion bondable to other polyolefins, and bonds with sufficient strength to adhesive tie layer polymers.

The outer layer 33 of the distal tip 30 comprises a relatively soft polymeric material, which preferably has a lower flexural modulus than the polymeric material forming the inner layer 31 of the distal tip 30. The polymeric material of the outer layer 33 typically has a Shore durometer hardness of not greater than about 63D, and a flexural modulus of about 10,000 to about 75,000 psi at room temperature. A presently preferred polymeric material for the outer layer 33 of the distal tip 30 is a polyether block amide (Pebax). Pebax is a polar polymer with a surface energy greater than 31 dynes/cm and a coefficient of friction (static) greater than 0.20. The polymeric material forming the outer layer 33 is preferably fusion bondable to the balloon 24, to facilitate attaching the distal tip 30 in the embodiment of FIG. 1 having the balloon distal skirt section 26 bonded to the outer surface of the distal tip 30. In an alternative embodiment, an outer sleeve member (not shown) is provided in place of the distal end of the balloon distal skirt section 26 and fusion bonded to the outer layer 33 of the distal tip 30.

The middle layer 32 of the distal tip 30 is typically a polymer which bonds to the polymeric materials of both the inner and outer layers 31, 33, so that the multiple layers of the distal tip 30 are sufficiently adhered together to not delaminate during use of the catheter 10. A variety of suitable polymers may be used for the middle layer 32 depending on the nature of the polymers of the inner and outer layers 31, 33. A presently preferred middle layer 32 polymer is an adhesive resin, including functionalized polyolefins such as Primacore and Plexar, and Lotader, Bynel and Licomont, which bond with sufficient strength to an HDPE inner layer 31.

The distal tip 30 is preferably formed by coextruding the multiple layers to form a coextruded multilayered tubular member which is then trimmed to the desired length. The length of the distal tip is typically about 2 to about 5 mm, and is significantly shorter than the total length of the inner tubular member 16 (i.e., about 1.5% to about 3.5% of the total length of the inner tubular member 16 in an over-the-wire type balloon catheter, or about 8% to about 20% of the total length of the inner tubular member in a rapid exchange type balloon catheter). As a result, the proximal end of the distal tip 30 is typically distal to the proximal skirt section 25 of the balloon 24, and is most preferably distal to the inflatable interior of the balloon 24.

In the illustrated embodiment, the inner tubular member 16 is a multilayered tube having an inner layer 34, middle layer 35, and outer layer 36. However, in alternative embodiments (not shown) the inner tubular member 16 is a single or dual layered tube. In one embodiment, the inner layer 34 of the inner tubular member 16 is the same polymeric material (e.g., HDPE) as the inner layer 31 of the distal tip 30, but the outer layer 36 of the inner tubular member 16 comprises a harder, less flexible polymeric material than the outer layer 33 of the distal tip 30 to provide the shaft with sufficient strength and push. As a result, the distal tip 30 has a lower composite modulus (i.e., average modulus of the multiple layers) than the inner tubular member 16. In one embodiment, the outer layer of the inner tubular member 16 is formed of a polymeric material having a Shore durometer hardness of greater than 70D, and more specifically about 75D to about 80D. In one presently preferred embodiment, the inner tubular member 16 has a Pebax outer layer 36 having a Shore durometer hardness of about 70D to about 80D, preferably about 72D, and the distal tip 30 has a Pebax outer layer 33 having a Shore durometer hardness of about 55D to about 63D. The middle layer 35 of the inner tubular member 16 is preferably an adhesive polymer as discussed above in relation to the distal tip middle layer 32, to bond the inner and outer layers 34, 36 together.

In a presently preferred embodiment, the inner layer 31 of the distal tip 30 consists of the non-polar, lubricious polymeric material without the presence of another polymer or an additive in the inner layer 31. However, in an alternative embodiment, the inner layer 31 comprises a polymer blended or doped with a non-polar additive.

The non-polar, lubricious inner surface of the distal tip inner layer 31 is preferably the result of the nature of the polymeric material forming the inner layer 31, and not the result of a surface treatment or coating. Thus, the wall of the inner layer, from the inner surface defining the distal tip lumen to the outer surface bonded to the middle layer 32, comprises a non-polar lubricious polymer. The thickness of the inner layer 31 is typically minimized relative to the thickness of the outer layer 33 to maximize flexibility. Thus, in one embodiment, the thickness of the inner layer 31 is less than the thickness of the outer layer 33, although in an alternative embodiment it is substantially equal to the thickness of the outer layer 33.

A distal tip formed in accordance with the invention having an inner layer of HDPE demonstrated improved performance compared with a distal tip formed of a polyamide. Specifically, dried or coagulated blood and contrast on a guidewire during testing was found to lift off the wire and form clumps in the polyamide distal tip. The clumped material would be transported distally until reaching the proximal edge of the hypotube section of the wire where most of the material would be deposited, causing resistance to guidewire movement. The distal tip having an HDPE inner layer did not pick up the dried or coagulated blood and contrast from the guidewire, so little or no accumulation of material was observed in the distal tip.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire type balloon catheter, the catheter of this invention may comprise a variety of intravascular catheters, such as guiding catheter, and rapid exchange type balloon catheters. Rapid exchange catheters generally comprise a shaft having a relatively short guidewire lumen extending from a guidewire distal port at the catheter distal end to a guidewire proximal port spaced a relatively short distance from the distal end of the catheter and a relatively large distance from the proximal end of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
 a) an elongated shaft having an inflation lumen and a guidewire lumen;
 b) a balloon on a distal shaft section with an interior in fluid communication with the inflation lumen; and
 c) a multilayered distal tip bonded to the catheter shaft at a distal end of the catheter by a bond joint, having an inner layer, an outer layer, and a different polymeric composition than a portion of the shaft which defines the guidewire lumen and which is proximally adjacent to the tip so that the tip is softer than the proximally adjacent shaft portion, wherein the bond joint includes a bond between the inner layer of the tip and the proximally adjacent shaft portion, and the inner layer of the tip comprises a polymeric material having a coefficient of friction and surface energy lower than the outer layer such that the inner layer has a lubricious, non-polar inner surface which is repulsive to polar liquids and which defines a lumen therein in communication with the guidewire lumen of the shaft.

2. The balloon catheter of claim 1 wherein the inner and outer layers of the distal tip are coextruded.

3. The balloon catheter of claim 1 wherein the distal tip includes a middle layer between the inner and outer layers, which bonds the inner layer to the outer layer.

4. The balloon catheter of claim 1 wherein the surface energy of the polymeric material of the inner layer of the distal tip is not greater than about 31 dynes/cm.

5. The balloon catheter of claim 1 wherein the surface energy of the polymeric material of the inner layer of the distal tip is about 17 to about 31 dynes/cm.

6. The balloon catheter of claim 1 wherein the coefficient of friction (static) of the polymeric material of the inner layer of the distal tip is not greater than about 0.20.

7. The balloon catheter of claim 1 wherein the polymeric material of the inner layer of the distal tip has a modulus of about 250 kpsi at room temperature.

8. The balloon catheter of claim 1 wherein the polymeric material of the inner layer of the distal tip is selected from the group consisting of polytetrafluoroethylene and high density polyethylene.

9. The balloon catheter of claim 1 wherein the portion of the shaft which is proximally adjacent to the distal tip has an outer layer with a higher modulus than the distal tip outer layer.

10. The balloon catheter of claim 1 wherein the outer layer of the distal tip is fusion bonded to another component of the catheter.

11. The balloon catheter of claim 10 wherein the other component is the balloon or an outer sleeve member.

12. The balloon catheter of claim 10 wherein the polymeric material of the outer layer of the distal tip is selected from the group consisting of polyether block amide copolymer, polyamide, and a polyurethane.

13. A balloon catheter, comprising:
 a) an elongated shaft comprising an outer tubular member defining an inflation lumen therein, and an inner tubular member within at least a section of the inflation lumen and defining a guidewire lumen therein, and the inner tubular member is a multilayered tube having an inner layer formed of high density polyethylene, and an outer layer formed of a polymeric material selected from the group consisting of a polyamide and a copolyamide;
 b) a balloon on a distal shaft section with an interior in fluid communication with the inflation lumen; and
 c) a multilayered distal tip bonded to and extending distally of a distal end of the multilayered inner tubular member at a distal end of the catheter, having a lubricious inner layer formed of high density polyethylene and defining a lumen therein in communication with the guidewire lumen, and an outer layer formed of a polymeric material having a higher coefficient of friction than the lubricious inner layer and which is selected from the group consisting of a polyamide and a copolyamide and which has a lower flexural modulus than the polymeric material forming the outer layer of the inner tubular member, so that the tip has a lower composite modulus than the inner tubular member.

14. The balloon catheter of claim 13 wherein the distal tip includes a middle layer between the inner and outer layers which bonds the distal tip inner layer to the distal tip outer layer.

15. The balloon catheter of claim 13 wherein the polymeric material forming the outer layer of the distal tip has a Shore durometer hardness of not greater than about 63D, and the polymeric material forming the outer layer of the inner tubular member has a Shore durometer hardness of not less than about 63D.

16. The balloon catheter of claim 15 wherein the Shore durometer hardness of the polymeric material forming the outer layer of the distal tip is not greater than about 55D.

17. A catheter, comprising:
 a) an elongated shaft having a lumen; and
 b) a distal tip bonded to the catheter shaft at a distal end of the catheter by a bond joint, having an inner layer, an outer layer, and a different polymeric composition than a portion of the shaft which defines the shaft lumen and which is proximally adjacent to the tip so that the tip is softer than the proximally adjacent shaft portion, wherein the bond joint includes a bond between the inner layer of the tip and the proximally adjacent shaft portion and the inner layer comprises a polymeric material having a static coefficient of friction of not greater than about 0.20 and a surface energy of not greater than about 31 dynes/cm, such that the inner layer has a lubricious, non-polar inner surface which is more lubricious than the outer layer of the tip and which is repulsive to polar liquids and which defines a lumen therein in communication with the lumen of the shaft.

18. The catheter of claim 17 wherein the distal tip inner layer is formed of high density polyethylene and the distal tip outer layer is formed of a polyamide copolymer or a polyetherurethane.

19. The catheter of claim 1 wherein the outer layer of the tip is thicker than the inner layer of the tip.

20. The catheter of claim 13 wherein the tip has a length which is shorter than the inner tubular member, and which is about 8% to about 20% of the inner tubular member length.

* * * * *